US012702418B2

(12) United States Patent
Gu et al.

(10) Patent No.: US 12,702,418 B2
(45) Date of Patent: Aug. 11, 2026

(54) BIONIC NERVE GRAFT AND PREPARATION METHOD THEREOF

(71) Applicant: NANTONG UNIVERSITY, Nantong (CN)

(72) Inventors: Xiaosong Gu, Nantong (CN); Xiu Dai, Nantong (CN); Xingzhong Gu, Nantong (CN); Leilei Gong, Nantong (CN); Meiyuan Li, Nantong (CN); Hualin Sun, Nantong (CN); Tianmei Qian, Nantong (CN); Hongkui Wang, Nantong (CN); Lai Xu, Nantong (CN)

(73) Assignee: NANTONG UNIVERSITY (CN)

( * ) Notice: Subject to any disclaimer, the term of this patent is extended or adjusted under 35 U.S.C. 154(b) by 0 days.

(21) Appl. No.: 18/551,556

(22) PCT Filed: Nov. 10, 2022

(86) PCT No.: PCT/CN2022/131041
§ 371 (c)(1),
(2) Date: Sep. 20, 2023

(87) PCT Pub. No.: WO2023/179045
PCT Pub. Date: Sep. 28, 2023

(65) Prior Publication Data

US 2025/0241646 A1 Jul. 31, 2025

(30) Foreign Application Priority Data

Oct. 18, 2022 (CN) ......................... 202211269678.0

(51) Int. Cl.
*A61B 17/11* (2006.01)
*A61B 17/00* (2006.01)
(Continued)

(52) U.S. Cl.
CPC .......... *A61B 17/1128* (2013.01); *A61L 27/34* (2013.01); *A61L 27/3633* (2013.01); *C12N 5/0669* (2013.01); *A61B 2017/00526* (2013.01)

(58) Field of Classification Search
CPC .......... A61L 27/18; A61L 27/20; C08L 71/02; C08L 5/08
See application file for complete search history.

(56) References Cited

U.S. PATENT DOCUMENTS

2014/0379009 A1* 12/2014 Yu ........................... A61L 27/56
264/108
2017/0182206 A1* 6/2017 Johnson ........... A61B 17/12022

FOREIGN PATENT DOCUMENTS

CN 1580255 A * 2/2005

OTHER PUBLICATIONS

English language translation of CN 1580255 A, Publ. Feb. 16, 2005. (Year: 2005).*

(Continued)

*Primary Examiner* — Dominic Lazaro

(57) ABSTRACT

A bionic nerve graft and a preparation method thereof is provided. The bionic nerve graft includes a helical stent, a nanofiber membrane, guide fibers and hBMSC-ECM. A surface of the helical stent is coated with the nanofiber membrane, the guide fibers and the hBMSC-ECM are placed in a tube cavity of the helical stent, and the raw materials of the helical stent, the nanofiber membrane and the guide fibers are all chitosan. The preparation method includes the following steps: preparing the helical stent by a mold pouring method, coating the surface of the helical stent with the nanofiber membrane by an electrostatic spinning method, preparing the guide fibers by a template method,
(Continued)

and filling the guide fibers and the hBMSC-ECM in the helical stent with the surface coated with the nanofiber membrane.

6 Claims, 8 Drawing Sheets

(51) Int. Cl.
*A61L 27/34* (2006.01)
*A61L 27/36* (2006.01)
*C12N 5/077* (2010.01)

(56) References Cited

OTHER PUBLICATIONS

Cai, S., et al., Directed Differentiation of Human Bone Marrow Stromal Cells to Fate-Committed Schwann Cells, Stem Cell Reports 9 (Oct. 10, 2017) pp. 1097-1108. (Year: 2017).*

* cited by examiner

BIONIC NERVE GRAFT AND PREPARATION METHOD THEREOF

FIELD

The present invention belongs to the technical field of biological materials, and in particular, relates to a bionic nerve graft and a preparation method thereof.

BACKGROUND

Peripheral nerve defect is a common clinical disease with poor prognosis and high disability rate, which seriously affects the quality of life of patients. At present, autotransplantation is still the "gold standard" for repairing the peripheral nerve defect. However, the clinical application of autotransplantation is limited by the problems of limited source of nerve donors, unmatched size of donor nerves and receptor nerves, and wrong nerve function bundles.

An objective of the invention is to provide an application of BMSC-Exos in treating PD. The BMSC-Exos can greatly improve a motor function of a model mouse with PD, protect dopaminergic neurons of the model mouse with PD, improve an olfactory function of the model mouse with PD, and also inhibit the activation of olfactory astrocytes of the model mouse with PD.

A tissue engineering scaffold material has the advantages of adjustable structural size, abundant material source and high processibility, and provides a new treatment method for the recovery of injured nerves. With the progress of a micro-nano manufacturing technology such as electrospinning, microetching, 3D printing and separation, bionic tissue engineering nerve grafts with porous structures, ordered structures, multi-channel structures, multi-layer structures or multi-branch structures have been constructed. In recent 20 years, in the construction process of the nerve graft, a large amount of research work shows that nerve tissue engineering scaffolds with a directional microstructure can induce the directional arrangement and growth of nerve cells (Rao Feng. Aligned chitosan nanofiber hydrogel grafted with peptides mimicking bioactive brain-derived neurotrophic factor and vascular endothelial growth factor repair long-distance sciatic nerve defects in rats. Theranostics, 2020, 10(4): 1590-1603). Although researchers have made some progress in the construction of the bionic tissue engineering nerve graft in recent years, the reconstruction of the microenvironment still has some challenges. No standard reconstruction scheme can achieve the perfect balance between the microenvironment stability and the functional reconstruction of the bionic nerve graft.

A natural biological material has the advantages of high biocompatibility, easy absorption and capability of promoting cell adhesion and proliferation, and has been widely applied to the preparation of a nerve regeneration graft. However, the natural biological material has poor mechanical property, which is easy to cause breakage and collapse, thereby greatly affecting the microenvironment stability of the regenerated nerves. Good mechanical property is necessary to maintain the microenvironment stability. To provide a sufficient mechanical support for the reconstruction of the regenerated nerve microenvironment, the mechanical property of the nerve graft can be improved by a method for adding a crosslinking agent or a synthetic macromolecule with excellent mechanical property. However, the crosslinking agent, particularly a chemical crosslinking agent, has high toxicity and is difficult to remove, and the biocompatibility of the synthetic macromolecule such as polycaprolactone (PCL) or polylactic acid (PLA) is far less than that of the natural material, so the crosslinking agent and the synthetic macromolecule are not conducive to the microenvironment reconstruction and the recovery of the nerve function. How to prepare the nerve graft with excellent mechanical property and excellent biocompatibility is a problem to be solved in the construction process of the bionic nerve graft.

SUMMARY

An objective of the present invention is to overcome the defects in the prior art and provide a bionic nerve graft and a preparation method thereof. The method is simple and low in cost. The prepared bionic nerve graft ensures sufficient mechanical support, provides a sufficient space for the transmission of nerve regeneration nutrients, and has high biocompatibility and low immunogenicity.

The present invention provides the following technical solutions:

according to a first aspect, a bionic nerve graft is provided and includes a helical stent, a nanofiber membrane, guide fibers and a human bone marrow stromal cell-extracellular matrix (hBMSC-ECM), where a surface of the helical stent is coated with the nanofiber membrane; the guide fibers and the hBMSC-ECM are placed in a tube cavity of the helical stent; and the raw materials of the helical stent, the nanofiber membrane and the guide fibers are all chitosan.

Further, the helical stent has an inner diameter of 1-6 mm, a length of 1-6 cm and a pitch of 0.5-5 mm.

Further, the guide fibers have a length of 1-3 cm, and the number of the guide fibers is 3-28.

According to a second aspect, a preparation method of the bionic nerve graft according to the first aspect is provided and includes the following steps:

using the chitosan as a raw material and preparing the helical stent by a mold pouring method;

using the chitosan as a raw material and coating the surface of the helical stent with one layer of nanofiber membrane to obtain a helical tube with a surface coated with the nanofiber membrane;

using the chitosan as a raw material and preparing the guide fibers by a template method; and filling the guide fibers and the hBMSC-ECM in the helical tube with the surface coated with the nanofiber membrane to obtain the bionic nerve graft.

Further, the step of preparing the helical stent includes:

preparing a chitosan solution with a concentration of 4 wt %-7 wt %;

pouring the chitosan solution on a threaded inner core mold;

placing the inner core mold with the chitosan solution into a NaOH solution of 5-20% for curing and shaping, and then performing washing with water, drying and demolding to obtain a helical stent semi-finished product; and immersing the helical stent semi-finished product into an acetic anhydride solution containing methanol of 5 wt % to perform acetylation for 6 h, performing fixation for 12 h by using the NaOH solution of 5-20%, and washing and drying to obtain the helical stent.

Further, the step of preparing the helical tube with the surface coated with the nanofiber membrane includes:

preparing a blended solution of the chitosan and polyethylene oxide with the total concentration of 3 wt %-5 wt %, the mass ratio of the chitosan to the polyethylene oxide being 100:(5-20);

placing the blended solution of the chitosan and the polyethylene oxide into an electrostatic spinning apparatus, placing the helical stent on a tubular receiving apparatus, performing electrostatic spinning, and coating the surface of the helical stent with one layer of nanofiber membrane; and placing the helical stent coated with the nanofiber membrane into a NaOH solution of 5-20% for curing and shaping, performing washing with water to remove the polyethylene oxide to obtain the helical tube with the surface coated with the nanofiber membrane.

Further, setting parameters of the electrostatic spinning include: a voltage is 5-35 kV, a flow velocity is 0.1-2 mL/h, a receiving distance is 5-35 cm, and a rotating speed of the receiving apparatus is 5-150 rpm.

Further, the step of preparing the guide fibers includes:

preparing a chitosan solution with a concentration of 4 wt %-7 wt %;

pouring the chitosan solution in a mold with a groove; and putting the mold with the chitosan solution into a NaOH solution of 5-20% for curing and shaping, and then performing washing with water, drying and demolding to obtain the guide fibers.

Further, the groove of the mold includes an inner groove and an outer groove which communicate with each other, the cross-sectional shape of the communicated inner groove and outer groove is shaped like an inverted Chinese character "Pin", a width of the outer groove is 100-500 μm, a height of the outer groove is 20-50 μm, a width of the inner groove is the same as the height of the outer groove, a height of the inner groove is 25-240 μm, the width of the outer groove is twice the sum of the height of the inner groove and the width of the inner groove, and the inner groove and the outer groove have the same length of 1-3 cm.

Further, the step of preparing the hBMSC-ECM includes:

coating a culture dish with a mesenchymal stem cell (MSC) adherent reagent diluted 100 times by a DPBS solution;

planting resuscitated human bone marrow stromal cell (hBMSC) into the coated culture dish, adding a complete culture medium, performing culture in a 5% $CO_2$ incubator at 37° C., and changing the culture medium once every two days; and when the cell saturation reaches 80%, using a complete culture medium containing ascorbic acid (50 μg/mL), changing the solution once every two days in a dark place, discarding the culture solution after ten days, performing washing with DPBS for three times, performing hypotonic operation with ultrapure water at 37° C. for 10 min, removing the ultrapure water, adding a cell lysis solution to perform reaction for 5 min, performing washing with DPBS, performing reaction by using DNA enzyme (0.1 mg/mL) at 37° C. for 2 h after washing, and finally, performing washing with DPBS and performing storage at 4° C.

Compared with the prior art, the present invention has the following beneficial effects:

(1) the bionic nerve graft provided by the present invention includes a helical stent, a nanofiber membrane, guide fibers and hBMSC-ECM, where a surface of the helical stent is coated by the nanofiber membrane, thereby ensuring that the bionic nerve graft has sufficient mechanical support and good compliance and provides a sufficient space for the transmission of nerve regeneration nutrients; the guide fibers and the hBMSC-ECM are placed in a tube cavity of the helical stent to play a good induction role, thereby facilitating the directional arrangement and growth of nerve cells; and nerve regeneration microenvironment elements are provided, thereby facilitating the regeneration of injured nerves.

(2) In the bionic nerve graft provided by the present invention, the raw materials of the helical stent, the nanofiber membrane and the guide fibers are all chitosan; the chitosan is a degradable natural material, has the advantages of high biocompatibility and low immunogenicity, and is conducive to the automatic step-by-step degradation of the nerve graft in the nerve repairing process; and the degradation product is completely absorbed by a human body, thereby avoiding immune tissue reaction.

(3) In the preparation method of the bionic nerve graft provided by the present invention, the helical stent is prepared by a mold pouring method, the surface of the helical stent is coated with one layer of nanofiber membrane by an electrostatic spinning method, and the mold pouring technology and the electrostatic spinning technology are combined, so that the bionic nerve graft can realize mechanical support and the transmission of the nerve regeneration nutrients at the same time, the total mass of the bionic nerve graft can be reduced, and the immunological rejection is greatly reduced.

(4) In the preparation method of the bionic nerve graft provided by the present invention, the technologies such as molding pouring, the template method and electrostatic spinning are simple and practicable, the cost is low, and the production process is safe and controllable.

DETAILED DESCRIPTION

The present invention is further described below with reference to the accompanying drawings. The following embodiments are only used for describing the technical solutions of the present invention more clearly, and are not intended to limit the protection scope of the present invention.

Embodiment 1

(1) Chitosan was dissolved in an acetic acid solution of 2% and was stirred for 30 min until being completely dissolved to obtain a chitosan solution with the concentration of 4 wt %; the chitosan solution was poured on a threaded inner core mold, where the inner mold has a length of 1 cm, a diameter of 2 mm, a thread pitch of 1 mm and a line width of 0.5 mm; the inner core mold with the chitosan solution was put into a NaOH solution of 5% for curing and shaping, was washed with water after being shaped, and was dried and demolded to obtain a helical stent semi-finished product; the helical stent semi-finished product was immersed into an acetic anhydride solution containing 5 wt % methanol for acetylation for 6 h, then was fixed for 12 h at room temperature by a NaOH solution of 5%, and was washed and dried to obtain a helical stent.

Figure 1:
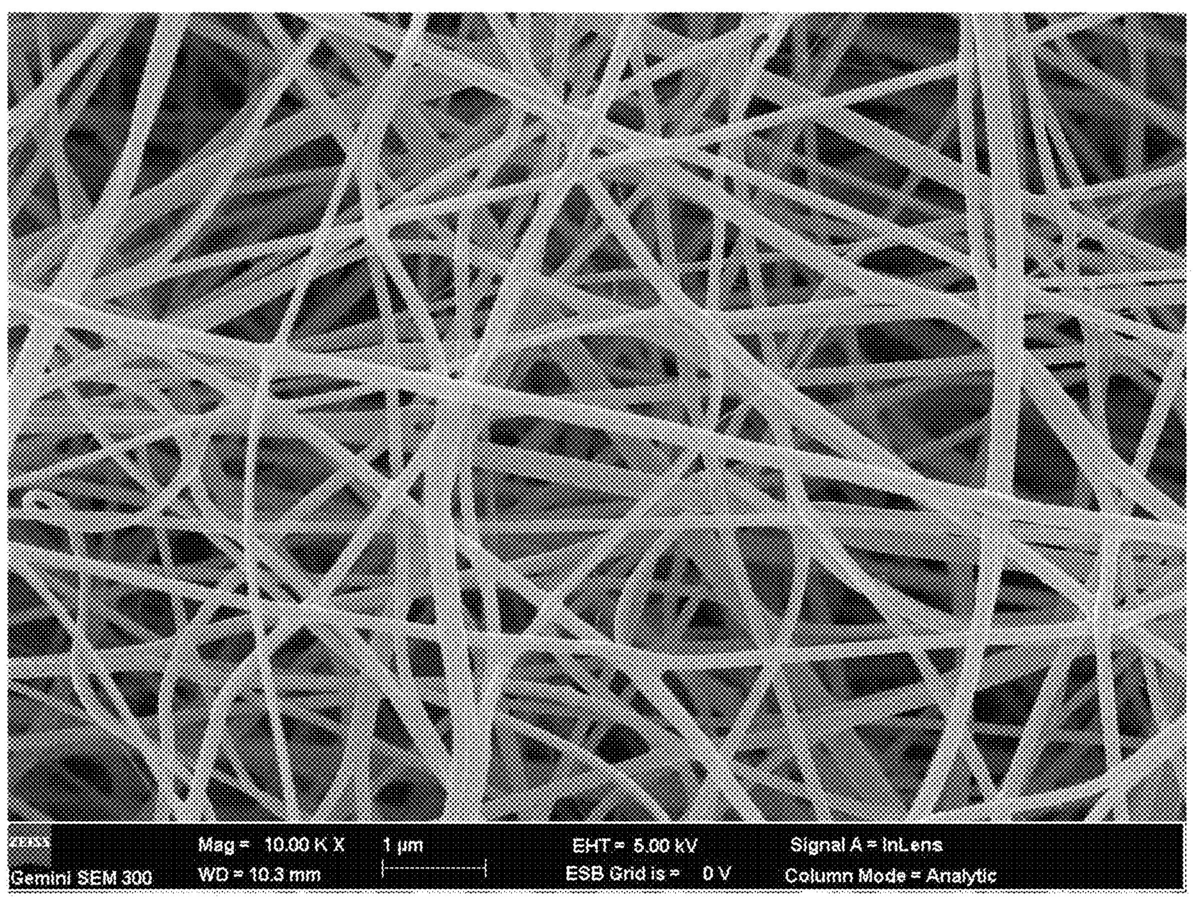
FIG. 1 is a scanning electron microscope (SEM) diagram of a nanofiber membrane in Embodiment 1.
Figure 2:
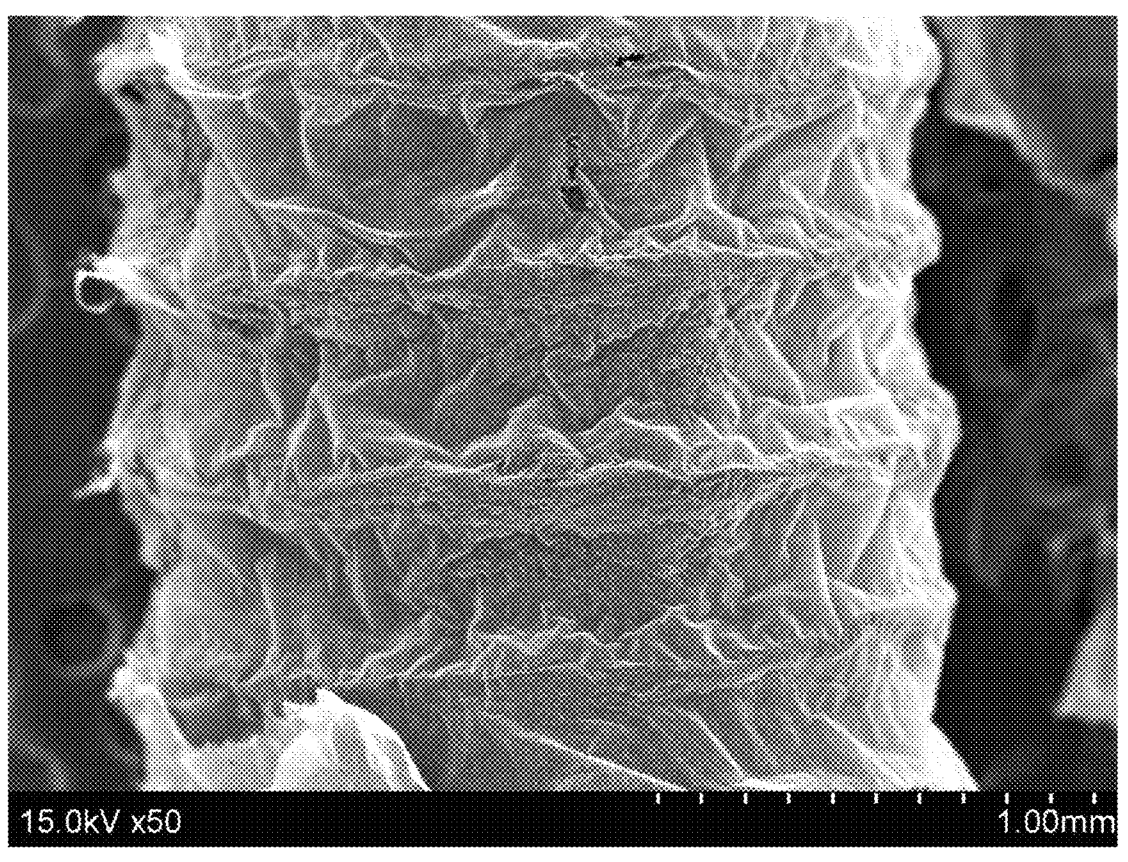
FIG. 2 is an SEM diagram of a helical tube with a surface coated with a nanofiber membrane in Embodiment 1.

(2) A proper amount of polyethylene oxide was dissolved into an acetic acid solution of 50%, and chitosan powder was added to prepare an electrostatic spinning solution, where the total concentration of the chitosan and the polyethylene oxide is 3 wt % and the mass ratio of the chitosan to the polyethylene oxide is 100:20; the helical stent was placed in a rotatable tubular receiving apparatus, the electrostatic spinning solution was put into an electrostatic spinning machine injector, a voltage was set to 5 kV, a flow velocity was set to 0.1 ml/h, a receiving distance was set to 5 cm, a rotating speed of the receiving apparatus was set to 5 rpm, electrostatic spinning was performed, and a surface of the helical stent was coated with one layer of nanofiber membrane (as shown in FIG. 1) to obtain a helical tube with a surface coated with the nanofiber membrane (as shown in FIG. 2).

Figure 3:
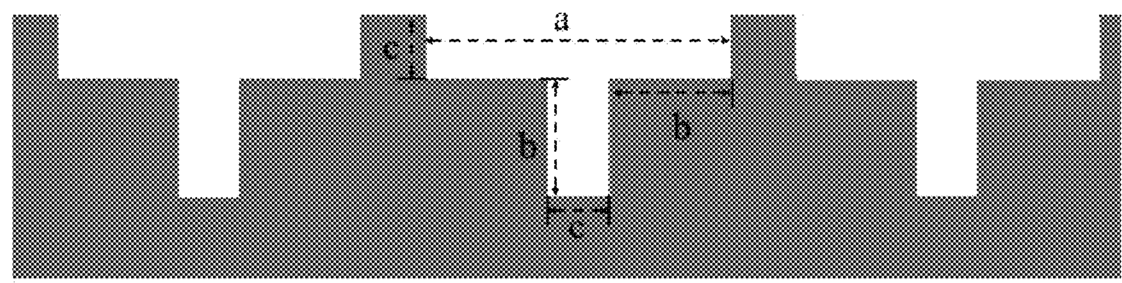
FIG. 3 is a schematic diagram of a sectional view of a mold groove for preparing guide fibers in an embodiment.

(3) The chitosan solution in step (1) was poured in a mold with a groove, where the groove includes an inner groove and an outer groove which communicate with each other, the cross-sectional shape is shown in FIG. 3, a length of the groove is 1 cm, a width a of the outer groove is 100 μm, a height e of the outer groove is 20 μm, the inner groove is located in the middle of the outer groove, a width of the inner groove is c, a height b of the inner groove is 40 μm, and the width of the outer groove is twice the sum of the height of the inner groove and the width of the inner groove. The mold with the chitosan solution was put into a NaOH solution of 10% for curing and shaping, was washed with water after being shaped, and was dried and demolded to obtain guide fibers.

(4) A culture dish was coated with an MSC adherent reagent diluted 100 times by a DPBS solution; resuscitated hBMSC was planted into the coated culture dish, a complete culture medium (a ratio of a NutriStem® MSC XF basic culture medium to a NutriStem® MSC XF additive is equal to 500 ml:3 ml) was added, culture was performed in a 5% $CO_2$ incubator at 37° C., and the culture medium was changed once every two days; and when the cell saturation reached about 80%, a complete culture medium containing ascorbic acid (50 μg/mL) was used, the solution was changed once every two days in a dark place, the culture solution was discarded after ten days, washing was performed with DPBS for three times, hypotonic operation was performed with ultrapure water at 37° C. for 10 min, the ultrapure water was removed, a cell lysis solution (3% TritonX-100, 2% lauryl sodium sulfate) was added to perform reaction for 5 min, washing was performed with DPBS, reaction was performed by using DNA enzyme (0.1 mg/mL) at 37° C. for 2 h after washing, and finally, washing was performed with DPBS for decellularization to obtain hBMSC-ECM.

(5) 28 guide fibers and the hBMSC-ECM were filled in the helical tube with the surface coated with the nanofiber membrane to obtain the bionic nerve graft, where the guide fibers are included in the tube wall of the helical stent.

Embodiment 2

(1) Chitosan was dissolved in an acetic acid solution of 2% and was stirred for 2 h until being completely dissolved to obtain a chitosan solution with the concentration of 6 wt %; the chitosan solution was poured on a threaded inner core mold, where the inner mold has a length of 4 cm, a diameter of 2 mm, a thread pitch of 1 mm and a line width of 0.5 mm; the inner core mold with the chitosan solution was put into a NaOH solution of 5% for curing and shaping, was washed with water after being shaped, and was dried and demolded to obtain a helical stent semi-finished product; the helical stent semi-finished product was immersed into an acetic anhydride solution containing 5 wt % methanol for acetylation for 6 h, then was fixed for 12 h at room temperature by a NaOH solution of 10%, and was washed and dried to obtain a helical stent.

(2) A proper amount of polyethylene oxide was dissolved into an acetic acid solution of 50%, and chitosan powder was added to prepare an electrostatic spinning solution, where the total concentration of the chitosan and the polyethylene oxide is 4 wt % and the mass ratio of the chitosan to the polyethylene oxide is 100:20. The helical stent was placed in a rotatable tubular receiving apparatus, the electrostatic spinning solution was put into an electrostatic spinning machine injector, a voltage was set to 20 kV, a flow velocity was set to 0.1 ml/h, a receiving distance was set to 15 cm, a rotating speed of the receiving apparatus was set to 100 rpm, electrostatic spinning was performed, and a surface of the helical stent was coated with one layer of nanofiber membrane to obtain a helical tube with a surface coated with the nanofiber membrane.

Figure 4:
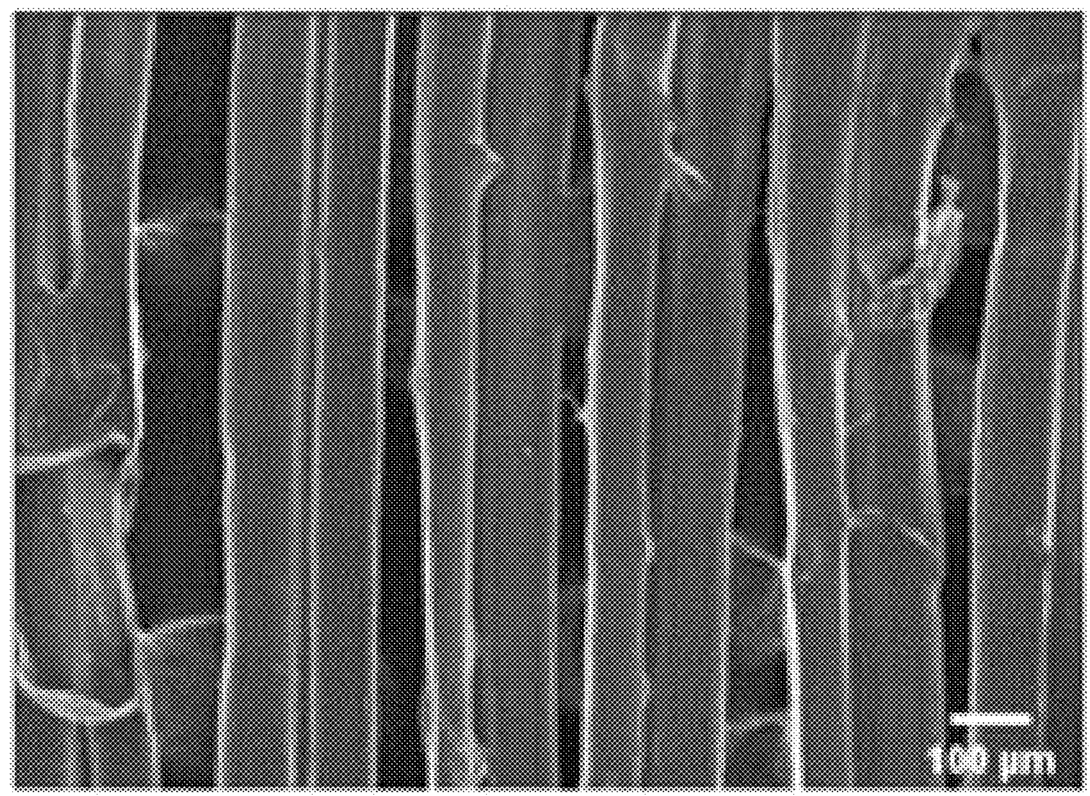
FIG. 4 is an SEM diagram of guide fibers in Embodiment 2.

(3) The chitosan solution in step (1) was poured in a mold with a groove, where the shape of the groove is the same as that in Embodiment 1, a length of the groove is 3 cm, a is 250 μm, b is 100 μm, and c s 50 μm; and the mold with the chitosan solution was put into a NaOH solution of 10% for curing and shaping, was washed with water after being shaped, and was dried and demolded to obtain guide fibers (as shown in FIG. 4).

(4) A culture dish was coated with an MSC adherent reagent diluted 100 times by a DPBS solution; resuscitated hBMSC was planted into the coated culture dish, a complete culture medium (a ratio of a NutriStem® MSC XF basic culture medium to a NutriStem® MSC XF additive is equal to 500 ml:3 ml) was added, culture was performed in a 5% $CO_2$ incubator at 37° C., and the culture medium was changed once every two days; and when the cell saturation reached about 80%, a complete culture medium containing ascorbic acid (50 μg/mL) was used, the solution was changed once every two days in a dark place, the culture solution was discarded after ten days, washing was performed with DPBS for three times, hypotonic operation was performed with ultrapure water at 37° C. for 10 min, the ultrapure water was removed, a cell lysis solution (3% TritonX-100, 2% lauryl sodium sulfate) was added to perform reaction for 5 min, washing was performed with DPBS, reaction was performed by using DNA enzyme (0.1 mg/mL) at 37° C. for 2 h after washing, and finally, washing was performed with DPBS for decellularization to obtain hBMSC-ECM.

(5) 5 guide fibers and the hBMSC-ECM were filled in the helical tube with the surface coated with the nanofiber membrane to obtain the bionic nerve graft, where the guide fibers are included in the tube wall of the helical stent.

Figure 5:
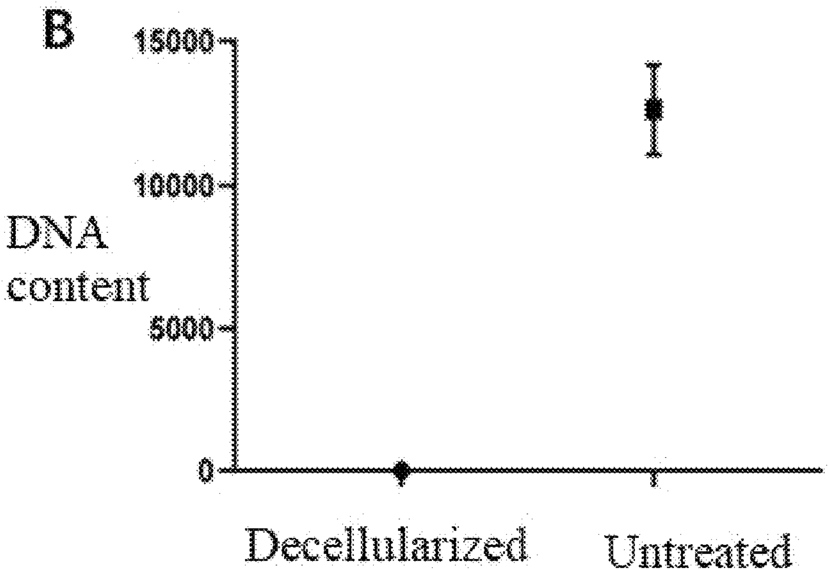
FIG. 5 is DNA content of hBMSCs-ECM before and after decellularization in Embodiment 2.
Figure 6:
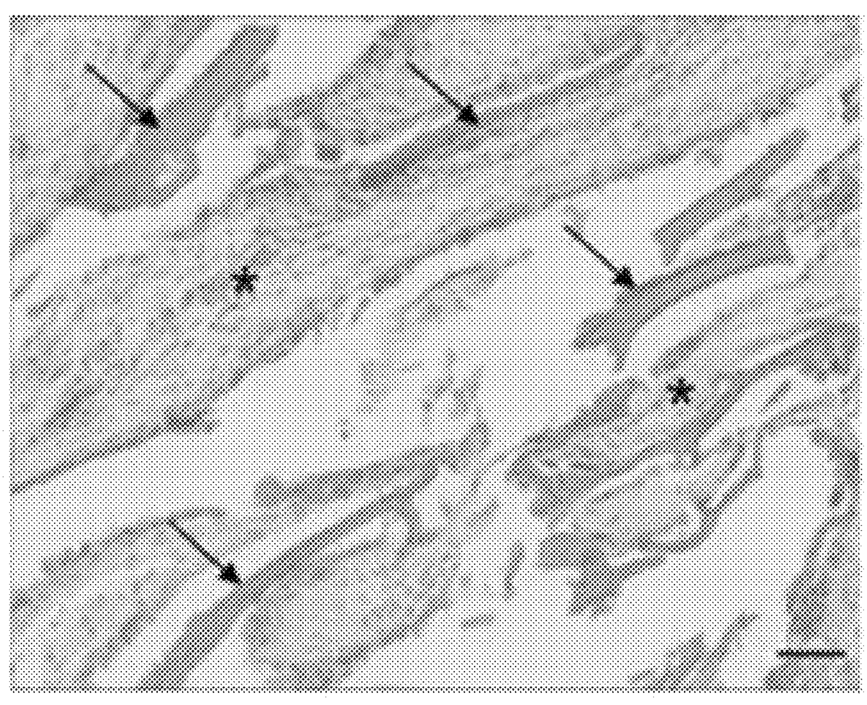
FIG. 6 is an HE staining diagram of 6-week in-vivo degradation of an acetylated helical stent in Embodiment 2.

The hBMSC-ECM in the bionic nerve graft prepared in this embodiment contains bioactive components capable of promoting nerve regeneration, such as fibronectin, laminin and collagen I, and almost no DNA can be detected (as shown in FIG. 5). After acetylation of the helical stent semi-finished product, the acetylation degree is increased from 4.73% to 74.77%, and high in-vivo degradability is achieved (as shown in FIG. 6). The diameter of the electrostatic spinning nanofiber membrane with which the outer layer is coated is about 100 nm.

Figure 7:
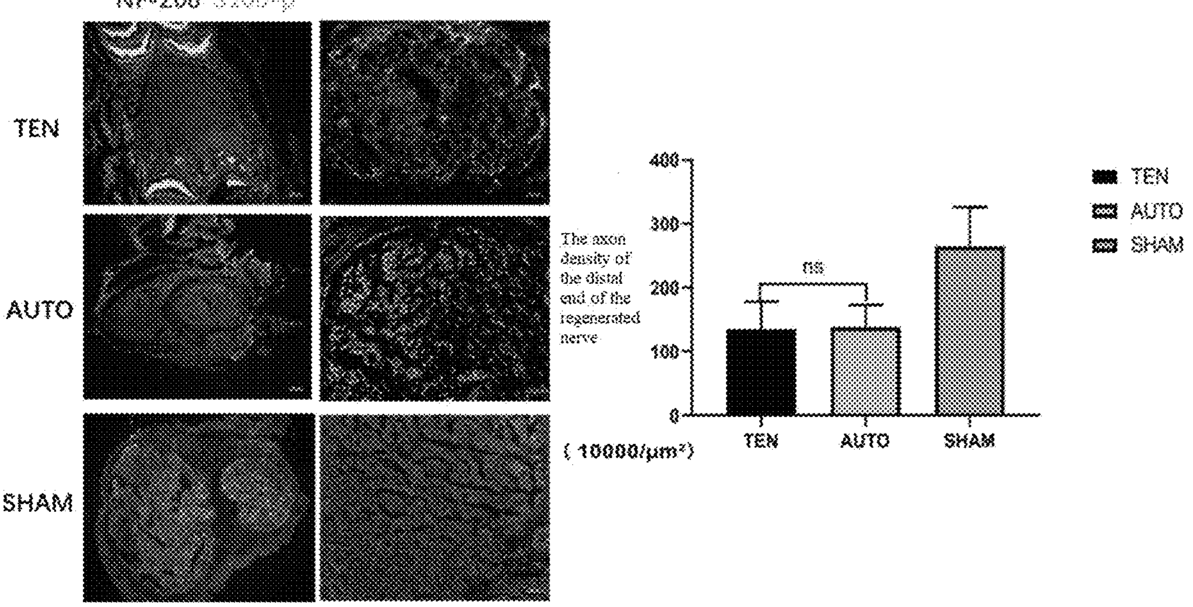
FIG. 7 is an immunofluorescence picture of a transverse section of a distal end of a regenerated nerve and an axon density of the distal end of the regenerated nerve obtained 8 weeks after a nerve graft in Embodiment 2 repairs a 10 mm sciatic nerve space of a rat (TEN: bionic nerve group, AUTO: autogenous nerve group, SHAM: sham-operation group, the same below)
Figure 8:
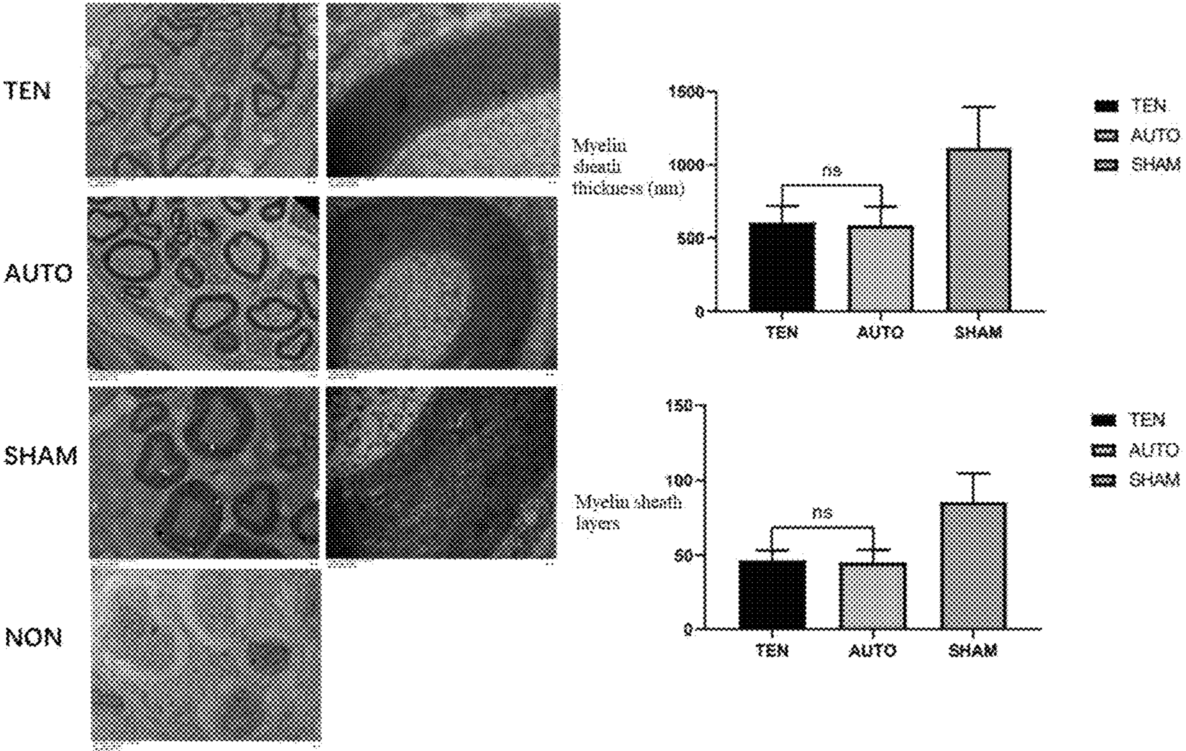
FIG. 8 is a transmission electron microscope (scale: left 50 μm, right 0.2 μm) of three groups of animal regenerated nerves obtained 12 weeks after operation in Embodiment 2, and a histogram of myelin sheath layers and myelin sheath thickness among the three groups.
Figure 9:
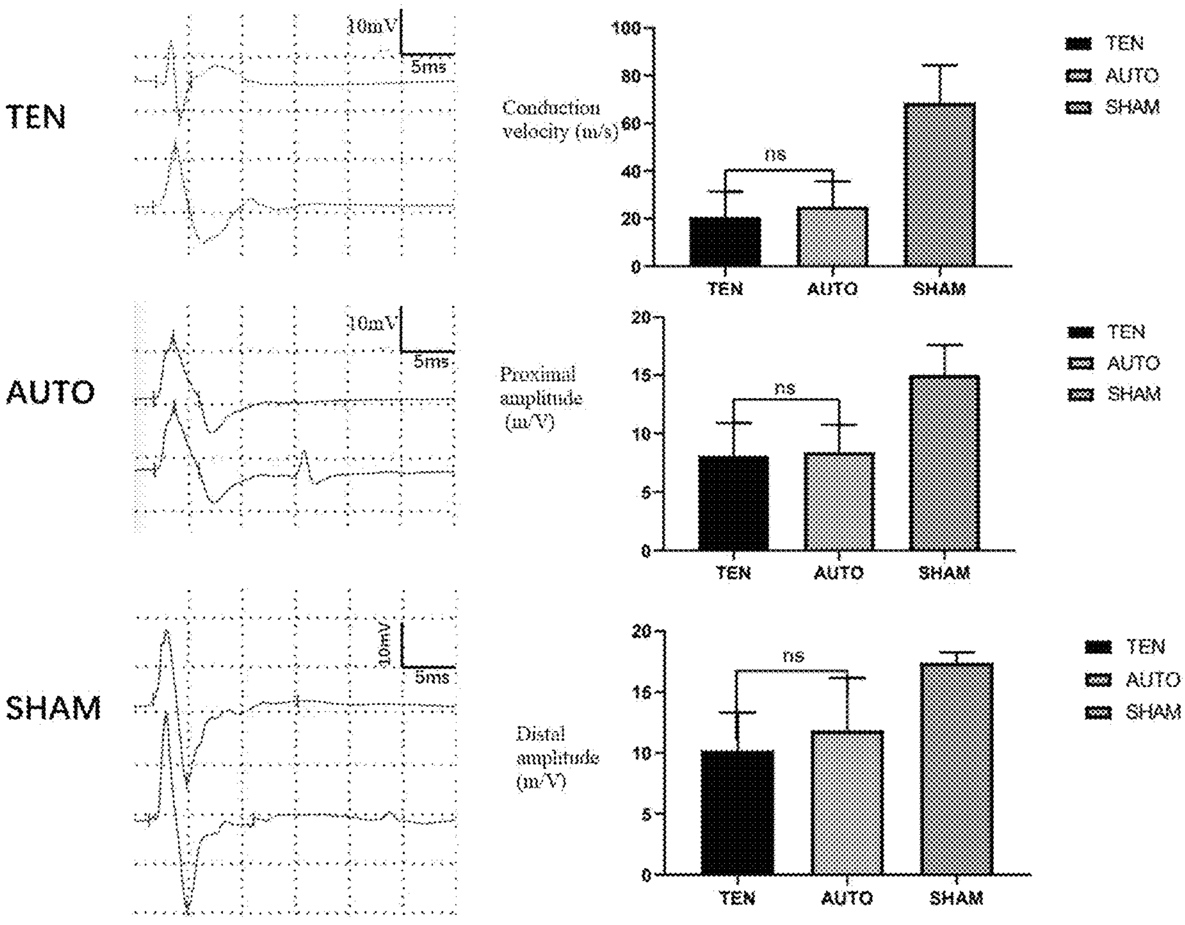
FIG. 9 is a composite muscle action potential diagram, conduction velocity, proximal amplitude and distal amplitude diagrams obtained 12 weeks after operation in Embodiment 2.
Figure 10:
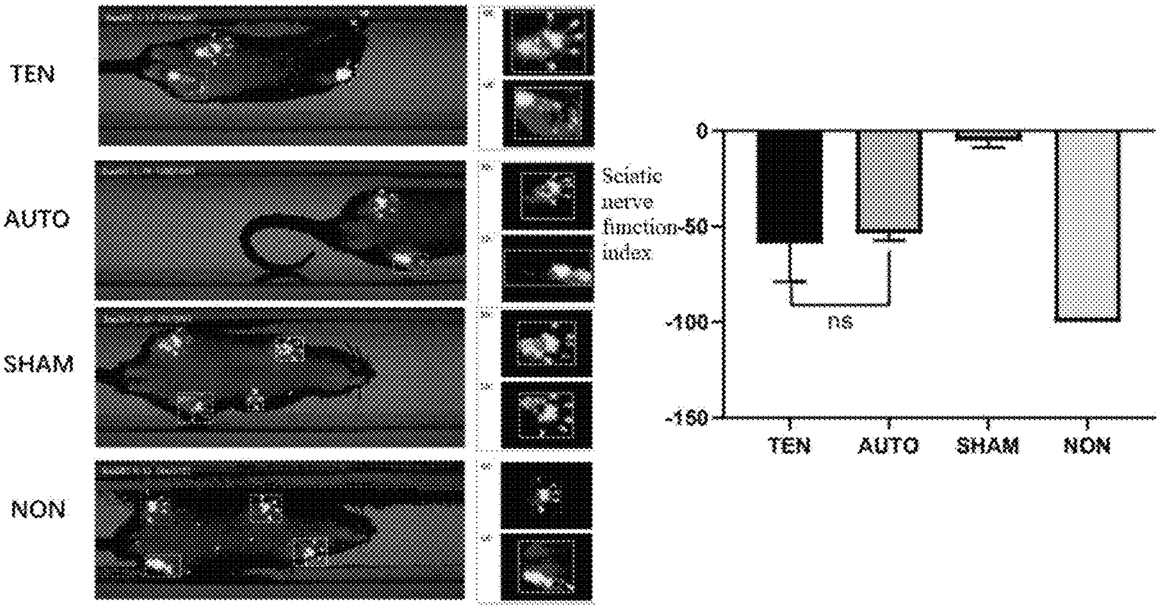
FIG. 10 is a CatWalk gait analysis diagram 12 weeks after operation in Embodiment 2.

The bionic nerve graft prepared in this embodiment is used to repair the 10 mm defect of the sciatic nerve of the rat. 8 weeks after the operation, the results of the immunofluorescence picture of the transverse section of the distal end of the regenerated nerve (as shown in FIG. 7) and the transmission electron microscope picture (as shown in FIG. 8) show that the bionic nerve graft has a good function of promoting nerve regeneration, and the effect of promoting nerve regeneration is equivalent to that of the autogenous nerve. 12 weeks after the operation, the function test (as shown in FIG. 9 and FIG. 10) shows that the bionic nerve has a good effect of repairing the injured nerve, and the repairing effect is similar to that of the autogenous nerve.

Embodiment 3

(1) Chitosan was dissolved in an acetic acid solution of 2% and was stirred for 4 h until being completely dissolved to obtain a chitosan solution with the concentration of 7 wt %; the chitosan solution was poured on a threaded inner core mold, where the inner mold has a length of 6 cm, a diameter of 5 mm, a thread pitch of 10 cm and a line width of 5 mm; the inner core mold with the chitosan solution was put into a NaOH solution of 20% for curing and shaping, was washed with water after being shaped, and was dried and demolded to obtain a helical stent semi-finished product; the helical stent semi-finished product was immersed into an acetic anhydride solution containing 5 wt % methanol for acetylation for 6 h, then was fixed for 12 h at room temperature by a NaOH solution of 20%, and was washed and dried to obtain a helical stent.

(2) A proper amount of polyethylene oxide was dissolved into an acetic acid solution of 50%, and chitosan powder was added to prepare an electrostatic spinning solution, where the total concentration of the chitosan and the polyethylene oxide is 5 wt % and the mass ratio of the chitosan to the polyethylene oxide is 100:5; the helical stent was placed in a rotatable tubular receiving apparatus, the electrostatic spinning solution was put into an electrostatic spinning machine injector, a voltage was set to 35 kV, a flow velocity was set to 2 ml/h, a receiving distance was set to 35 cm, a rotating speed of the receiving apparatus was set to 150 rpm, electrostatic spinning was performed, and a surface of the helical stent was coated with one layer of nanofiber membrane to obtain a helical tube with a surface coated with the nanofiber membrane.

(3) The chitosan solution in step (1) was poured in a mold with a groove, where the shape of the groove is the same as that in Embodiment 1, a length of the groove is 1 cm, a is 500 μm, b is 225 μm, and e is 50 μm; and the mold with the chitosan solution was put into a NaOH solution of 20% for curing and shaping, was washed with water after being shaped, and was dried and demolded to obtain guide fibers.

(4) A culture dish was coated with an MSC adherent reagent diluted 100 times by a DPBS solution; resuscitated hBMSC was planted into the coated culture dish, a complete culture medium (a ratio of a NutriStem® MSC XF basic culture medium to a NutriStem® MSC XF additive is equal to 500 ml:3 ml) was added, culture was performed in a 5% $CO_2$ incubator at 37° C., and the culture medium was changed once every two days; and when the cell saturation reached about 80%, a complete culture medium containing ascorbic acid (50 μg/mL) was used, the solution was changed once every two days in a dark place, the culture solution was discarded after ten days, washing was performed with DPBS for three times, hypotonic operation was performed with ultrapure water at 37° C. for 10 min, the ultrapure water was removed, a cell lysis solution (3% TritonX-100, 2% lauryl sodium sulfate) was added to perform reaction for 5 min, washing was performed with DPBS, reaction was performed by using DNA enzyme (0.1 mg/mL) at 37° C. for 2 h after washing, and finally, washing was performed with DPBS for decellularization to obtain hBMSC-ECM.

(5) 3 guide fibers and the hBMSC-ECM were filled in the helical tube with the surface coated with the nanofiber membrane to obtain the bionic nerve graft, where the guide fibers are included in the tube wall of the helical stent.

The foregoing descriptions are only preferred implementation manners of the present invention. It should be noted that for a person of ordinary skill in the art, several improvements and modifications may further be made without departing from the technical principle of the present invention. These improvements and modifications should also be deemed as falling within the protection scope of the present invention.

What is claimed is:

1. A preparation method of a bionic nerve graft which comprises a helical stent, a nanofiber membrane, guide fibers and hBMSC-ECM (human-derived Bone Mesenchymal Stem Cell-Extracellular Matrix), wherein a surface of the helical stent is coated with the nanofiber membrane; the guide fibers and the hBMSC-ECM are placed in a tube cavity of the helical stent; and the helical stent, the nanofiber membrane and the guide fibers are formed of chitosan; wherein the preparation method comprises the following steps:

providing the chitosan and forming the helical stent by a mold pouring method;

providing the chitosan and coating the surface of the helical stent with one layer of nanofiber membrane in order to obtain a helical tube with a surface coated with the nanofiber membrane;

providing the chitosan and forming the guide fibers by a template method; and filling the helical tube with the surface coated with the nanofiber membrane with the guide fibers and the hBMSC-ECM in order to obtain the bionic nerve graft;

wherein the step of forming the guide fibers comprises:

providing a chitosan solution with a concentration of 4 wt % to 7 wt %;

pouring the chitosan solution into a mold with a groove; and putting the mold with the chitosan solution into a NaOH solution of 5 to 20% for curing and shaping, and washing with water, drying and demolding in order to obtain the guide fibers.

2. The preparation method of the bionic nerve graft according to claim 1, wherein the mold pouring method of forming the helical stent comprises:

providing a chitosan solution with a concentration of 4 wt % to 7 wt %;

pouring the chitosan solution on a threaded inner core mold;

placing the inner core mold with the chitosan solution into a NaOH solution of 5 to 20% for curing and shaping, and then washing with water, drying and demolding in order to obtain a helical stent semi-finished product; and immersing the helical stent semi-finished product into an acetic anhydride solution containing methanol of 5 wt % to perform acetylation for 6 hours, performing fixation for 12 hours by using the NaOH solution of 5 to 20%, washing and drying in order to obtain the helical stent.

3. The preparation method of the bionic nerve graft according to claim 1, wherein the step of preparing the helical tube with the surface coated with the nanofiber membrane comprises:

preparing a blended solution of the chitosan and polyethylene oxide with the total concentration of 3 wt % to 5 wt %, wherein the mass ratio of the chitosan to the polyethylene oxide is 100:5 to 100:20;

placing the blended solution of the chitosan and the polyethylene oxide into an electrostatic spinning apparatus, placing the helical stent on a tubular receiving apparatus, performing electrostatic spinning, and coating the surface of the helical stent with one layer of nanofiber membrane; and placing the helical stent coated with the nanofiber membrane into a NaOH solution of 5 to 20% for curing and shaping, followed by washing with water to remove the polyethylene oxide in order to obtain the helical tube with the surface coated with the nanofiber membrane.

4. The preparation method of the bionic nerve graft according to claim 3, wherein setting parameters of the electrostatic spinning comprise a voltage of 5 to 35 kV, a flow velocity of 0.1 to 2 mL/h, a receiving distance of 5 to 35 cm, and a rotating speed of the receiving apparatus of 5 to 150 rpm.

5. The preparation method of the bionic nerve graft according to claim 1, wherein the groove of the mold comprises an inner groove and an outer groove which communicate with each other, wherein a cross-sectional shape of the communicated inner groove and outer groove features the inner groove is located in the middle of the outer groove; wherein a cross-sectional width of the outer groove is 100 to 500 μm, a cross-sectional height of the outer groove is 20 to 50 μm, a cross-sectional width of the inner groove is the same as the cross-sectional height of the outer groove, a cross-sectional height of the inner groove is 25 to 240 μm, the cross-sectional width of the outer groove is twice the sum of the cross-sectional height of the inner groove and the cross-sectional width of the inner groove, and the inner groove and the outer groove have the same length of 1 to 3 cm.

6. The preparation method of the bionic nerve graft according to claim 1, wherein the hBMSC-ECM is obtained by a process comprising:

coating a culture dish with an Mesenchymal Stem Cell (MSC) adherent reagent diluted 100 times by Dulbecco's Phosphate-Buffered Saline (DPBS) solution;

planting resuscitated human-derived Bone Mesenchymal Stem Cell (hBMSC) into the coated culture dish, adding a complete culture medium, performing culture in a 5% $CO_2$ incubator at 37° C., and changing the culture medium once every two days; and changing with a complete culture medium containing ascorbic acid when cell saturation reaches 80%, changing the solution once every two days in a dark place, discarding the culture solution after ten days, washing with DPBS three times, performing hypotonic operation with ultrapure water at 37° C. for 10 minutes, removing the ultrapure water, adding a cell lysis solution to perform reaction for 5 minutes, washing with DPBS, treating with DNA enzyme at 37° C. for 2 hours after washing, washing with DPBS, and storing at 4° C.

* * * * *